United States Patent [19]

Amer

[11] Patent Number: 4,963,346

[45] Date of Patent: Oct. 16, 1990

[54] METHOD AND COMPOSITION FOR TREATMENT OR PREVENTION OF DENTAL PLAQUE CALCULUS AND GINGIVITIS

[75] Inventor: M. Samir Amer, Montecito, Calif.

[73] Assignee: Amer & Company, Inc., Montecito, Calif.

[21] Appl. No.: 200,681

[22] Filed: May 31, 1988

[51] Int. Cl.$^5$ .......................... A61K 7/16; A61K 7/26; A61K 31/56; A01N 45/00

[52] U.S. Cl. ........................................ 424/49; 424/58; 514/169; 514/170; 514/171

[58] Field of Search .................... 424/49, 58; 514/169, 514/170, 171

[56] References Cited

U.S. PATENT DOCUMENTS

| | | | |
|---|---|---|---|
| 3,828,106 | 8/1974 | Rudel | 514/170 |
| 3,865,939 | 2/1975 | Jandacek | 514/182 |
| 3,988,433 | 10/1976 | Benedict | 424/53 |
| 4,083,955 | 4/1978 | Grabenstetter et al. | 424/49 |
| 4,115,313 | 9/1978 | Lyon et al. | 424/64 |
| 4,224,319 | 9/1980 | Marcadet | 514/171 |
| 4,472,373 | 9/1984 | Ryan | 424/54 |
| 4,716,035 | 12/1987 | Sampathkumar | 424/52 |

FOREIGN PATENT DOCUMENTS 1183126  2/1985 Canada.

OTHER PUBLICATIONS

Fourel et al., "Essais Cliniques de L'unsaponifiable D'Huile de Germe de Mais en Parodontologie," L'Information Dentaire 1967, 8, 3–7.

Ozick, "Clinical Evaluation of the Effect of a Systemic Agent (W-1963) on Periodontal Disease," Oral Surgery, Oral Medicine and Oral Pathology, 1969, 27, 319–322.

Berkenbaum et al., "Quelques Resultats de L'Experimentation de L'extrait Insaponifiable de Mais de Les parodontolyses," Revue Medicale de Bruxelles, 1969, 4, 213–220.

Chaput et al., "Action De L'Indasal sur las Parodontolyse Experimentale du Hamster," Ext. de la Revue Francaise d'Odonto-Stomatologie Tome XVIII-1971, 9, 1145–1154.

Tecucianu, "Etude Experimentale par la Methode a Double Insu d'une Pate Gingivale a Base d'insaponifiable de Mais," L'Information Dentaire, 1972, 45, 1–8.

Migozzi et al., "Etude de L'Action Therapeutique de L'Extrait Titre de L'Insaponifiable de Zea Mays L au Cours de la Pose des Prosthesis Amovibles," Chirurgien-Dentiste de France 1973, 3, 1–5.

Kerebel et al., "Etude Ultrastructurale d'une Therapeutique des Parodontolyses Experimentales Chez le Hamster Dore'," Rev. Mens. Suisse Odonto-Stomatologie 1974, 84, 155–165.

Colombel et al., "Trial of the Unsaponified Fraction of Zea Mays L on 'Dryness of the Mouth' Induced by Psychotropic Drugs," Progres Odonto-Stomatologique, 12, 31–33, 1974.

Tecucianu, "Etude Clinique a Double Insu de L'Extractum Titre de la Fraction Insaponifiable de Zea Mays L sur L'inflammation Gingivale," l'Information Dentaire, 1975, 27, 1–12.

Kerebel et al., "Etude Semi-Quantitative des Parodontolyses et des Reparations Osseuses Experimentales Chez de Hamster Dore," J. Biol. Buccale, 1977, 5, 77–84.

Bailly, "Un Traitement des Secheresses Buccales Post--Therapeutiques: L'Extrait Titre de la Fraction Insaponifiable de Zea Mays L.," Progres Medicale 1978, 108, 473-475.

Porte et al., "Clinical and Ultrastructural Study of the Action of Corn Oil Insaponifiable In the Course of Human Periodontal Disease," Extrait des Actualities Odonto-Stomatologiques, 1978, 121, 1–15.

Bellot et al., "Treatment of Chronic Periodontitis," Extract de la Vie Medicale 1979, 16, 1355–1363.

Son, "Influence of Standard Extract of the Unsaponifiable Fraction of Zea Mays L on Periodontal Disease," Dental Science and Research, 1982, 8, 895–901.

Package Insert for "Kayadent" toothpaste made in Spain.

Package Insert for "Insadol" drinkable solution and sugar coated tables, made in France.

*Primary Examiner*—Nathan M. Nutter
*Attorney, Agent, or Firm*—St. Onge Steward Johnston & Reens

[57] ABSTRACT

A method and composition is presented for the treatment or prevention of dental plaque, calculus and gingivitis. The method comprises either systemically or topically treating the oral cavity for a therapeutically or prophylactically effective time with a therapeutically or prophylactically effective amount of a treatment composition which comprises phytosterols.

29 Claims, No Drawings

METHOD AND COMPOSITION FOR TREATMENT OR PREVENTION OF DENTAL PLAQUE CALCULUS AND GINGIVITIS

DESCRIPTION

1. Technical Field

The present invention relates to a method and composition which is effective for the treatment or prevention of dental plaque, calculus and gingivitis and other periodontal diseases of the oral cavity. The method comprises the systemic or topical treatment of the oral cavity with a treatment composition, especially the topical application of the treatment composition to the surfaces of the oral cavity, i.e., the gums and teeth, to be treated.

Plaque, calculus and gingivitis are dental conditions which have long been the cause of great concern to dentists and other oral physicians and which can, if left untreated, lead to loss of supporting bone and tissue and ultimately to loss of a patient's tooth or teeth. Plaque, the most common of the three, is described as a gelatinous microbial formation or growth on a tooth or teeth. Calculus is most often described as a concretion or hard inorganic mass on a tooth or teeth. Gingivitis, generally considered the most serious of the three, can be simply described as an inflammation of the gums, i.e., soft tissue supporting teeth.

Treatments for dental plaque, calculus and gingivitis by dentists and other oral physicians on an in-office bases are known and are generally thought to be effective. Such treatments have several drawbacks because of their expense, inconvenience and discomfort to the patient. Moreover, these treatments are designed for the therapeutic treatment of plaque, calculus and gingivitis, as opposed to prevention of these diseases. What is needed, therefore, is a treatment which can be performed by a patient which is inexpensive, convenient and provides prophylactic as well as therapeutic benefits.

2. Background Art p The use of sterols for therapeutic or other health-related reasons has been known for some time. For instance, Jandacek, in U.S. Pat. No. 3,865,939, teaches the use of a minor amount of sterols (2.0 to 6.0 weight percent) in cooking and salad oil compositions to impart hypocholesterolemic properties to the oils. In another application of sterols, Marcadet in U.S. Pat. No. 4,224,319 describes an antiseptic composition useful against bromidrosis which preferably includes about 0.02 to about 0.5 weight percent of sterols. The composition of Marcadet is topically applied to affected areas of the skin, especially the feet.

It has also been found that the unsaponifiable fraction of corn oil extracted by Zea Mays L, used under the tradename Insadol by Laroche Navarron Laboratories of Puteaux, France, which comprises sterols, when administered in either solution or tablet form is useful in the treatment of mouth dryness induced by psychotropic drugs. This effect was described by Doctors J. Cl. Colombel and Cl. Parente in "Trial of the Unsaponifiable Fraction of Zea Mays L on 'Dryness of the Mouth' Induced by Psychotropic Drugs", Progres Odonto-Stomatologique, 12, 31-33, 1974.

The use of the titrated unsaponifiable fraction of maize germ oil in the treatment of periodontal disease is studied by Scopp, Kumar, Kassouny and Ozick in "Unsaponifiable Corn Oil Fraction in the Treatment of Periodontal Disease/A Clinical and Histologic Evaluation Using A Double Blind Technique". Drs. Scopp et al. studied a fraction which consisted of 18 to 25% phytosterols and which was administered by systemic ingestion in tablet form. The study found that treatment with the titrated unsaponifiable fraction results in a decrease in gingival inflammation.

A later study by Ozick, "Clinical Evaluation of the Effect of a Systemic Agent (W-1963) on Periodontal Disease", O.S., O.M. & O.O., Vol. 27, No. 3, March 1969, studied the effect of treatment with tablets containing the titrated unsaponifiable fraction of corn germ oil, containing 18 to 25% phytosterols, on periodontal disease. The study concluded that the systemic treatment of periodontal disease with the titrated unsaponifiable fraction of corn germ oil will lead to improvement in the disease.

Unfortunately, the systemic treatment of periodontal and dental conditions such as plaque, calculus and gingivitis with such low levels of phytosterols left much to be desired in terms of their effectiveness at the therapeutic site or at prophylactically treating these diseases and did not recognize the benefits of either systemic or topical treatment with high levels of phytosterols.

DISCLOSURE OF INVENTION

The present invention relates to a treatment composition and a method of use of the treatment composition for the treatment or prevention of dental plaque, calculus or gingivitis comprising either systemically or topically treating the oral cavity for a therapeutically or prophylactically effective time with a therapeutically or prophylactically effective amount of the treatment composition which comprises phytosterols. This invention further relates to a method of making the treatment composition.

The composition which comprises the treatment composition of the present invention comprises phytosterols, as noted above. More preferably, the composition consists essentially of phytosterols, by which is meant at least about 80% of phytosterols, more preferably at least about 94% of phytosterols, and most preferably at least about 99% of phytosterols. Advantageously, when topical treatment is desired, a normally non-ingested carrier suitable for delivery of the treatment composition to the surfaces of the oral cavity is also present and associated with the composition. The use of the present invention is in the treatment or prevention of dental plaque, calculus or gingivitis of humans and animals, hence the treatment composition of this invention is applied either systemically or topically to the oral cavities of humans and animals.

BEST MODE FOR CARRYING OUT THE INVENTION

Composition

The treatment composition of the present invention generally comprises at least about 80% of phytosterols. Most preferably, the treatment composition comprises as high as about 94% and even 99% and higher of phytosterols. Phytosterols are plant steroid alcohols, containing the common steroid nucleus, generally a fused, reduced 17-carbon atom ring system, cyclopentanoperhydrophenanthrene, plus an 8- to 10-carbon atom side chain and a hydroxyl group. The phytosterols fraction of this invention generally comprises a mixture of sitosterol, divided into alphasitosterol (4-methyl-stigmasta-7,24(28)-dien-3-ol), beta-sitosterol (stigmast-5-en-3-ol)

and gamma-sitosterol ((24S)-stigmast-5-en-3beta-ol); campesterol ((24R)-ergost-5-en-3beta-ol); and stigmasterol (stigmasta-5,22-dien-3beta-ol). Other useful phytosterols include brassicampesterol and sterol esters.

Although the treatment composition may comprise only a single phytosterol, the treatment composition will more typically comprise a plurality of phytosterols, as noted above. Advantageously, the treatment composition comprises at least about 40% by weight of sitosterol (or any mixture of alpha-, beta- or gamma-sitosterol), most preferably about 40% to about 60% by weight of sitosterol; about 20% to about 45% by weight of campesterol, most preferably about 20% to about 33% by weight of campesterol; and about 3% to about 26% by weight of stigmasterol, most preferably about 15% to about 25% by weight of stigmasterol.

a. Composition for Topical Treatment

As noted, the treatment composition of the present invention can be associated with a normally non-ingested carrier suitable for delivery of the treatment composition to the surfaces of the oral cavity for topical treatment. Besides being capable of delivery of the treatment composition and, hence, compatible with the treatment composition, the carrier should most preferably also be pharmaceutically-acceptable since it is being applied to the oral cavity of humans and animals. The term "normally non-ingested" as used herein refers to a carrier which is intended to be retained in the oral cavity for a sufficient time for the treatment composition to be therapeutically or prophylactically effective, rather than just immediately ingested. In most cases, the carrier is expelled from the oral cavity after such time, but in some situations, the carrier can be ingested after retention in the oral cavity and topical application to the surfaces thereof for the required time. The term "compatible" as used herein refers to a carrier which, when commingled with the treatment composition of this invention, is substantially inert with respect to the properties of the treatment composition which provide the therapeutic or prophylactic treatment of dental plaque, calculus or gingivitis, i.e., the carrier does not interact with the treatment composition to significantly reduce the therapeutic or prophylactic properties of the treatment composition. The term "pharmaceutically-acceptable" as used herein refers to a carrier which is of sufficiently high purity and low toxicity to render it acceptable for application to the surfaces of the oral cavities of humans or animals.

Suitable carriers can include by way of example the conventional components of any of the following: toothpaste, toothpaste gels, tooth powders, tooth polishes, creams or mousses, ointments, mouthwashes, mouth sprays or aerosols, mouth rinses, effervescent solutions, chewing gums, dental floss and coatings therefore, lozenges and candies. Such components generally include surfactants, flavoring agents, sweeteners, abrasives, humectants, sudsing agents, chelating agents, buffers, fluoride-containing agents, antiseptics, germicides, astringents, thickeners, coloring agents, emulsifiers, water, alcohols, effervescing agents, gums, dental floss and mixtures thereof.

The treatment composition of the present invention is generally associated with the carrier such that the treatment composition comprises about 0.25% to about 25.0% by weight of the total of the treatment composition and carrier combination. The treatment composition preferably comprises about 0.5% to about 6.0% by weight of the total and most preferably comprises about 1.0% up to about 5.0% by weight of the total. The carrier advantageously makes up the balance.

Exemplary of carrier/treatment composition formulations which can be used according to this invention are the following:

| | | |
|---|---|---|
| 1. | dibasic calcium phosphate, dihydrate | 50.00% |
| | glycerin | 20.00 |
| | mineral oil | 3.75 |
| | sodium carboxymethyl cellulose | 1.00 |
| | sodium lauryl sulfate | 1.00 |
| | treatment composition | 1.00 |
| | flavorings | 0.70 |
| | sweetener | 0.10 |
| | sodium fluoride | 0.10 |
| | water | bal. |
| 2. | dibasic calcium phosphate, dihydrate | 50.00% |
| | sorbitol | 10.00 |
| | glycerin | 10.00 |
| | mineral oil | 3.75 |
| | sodium lauryl sulfate | 2.00 |
| | ethanol | 2.00 |
| | sodium carboxymethyl cellulose | 1.00 |
| | treatment composition | 1.00 |
| | sodium monofluorophosphate | 0.30 |
| | sweetener | 0.10 |
| | eugenol | 0.05 |
| | water | bal. |
| 3. | calcium carbonate | 50.00% |
| | glycerin | 20.00 |
| | mineral oil | 3.75 |
| | sweetener | 2.10 |
| | sodium carboxymethyl cellulose | 1.00 |
| | lauryl diethanolamide | 1.00 |
| | treatment composition | 1.00 |
| | flavoring | 0.80 |
| | water | bal. |
| 4. | dibasic calcium phosphate, dihydrate | 50.00 |
| | glycerin | 20.00 |
| | mineral oil | 3.75 |
| | sodium carboxy cellulose | 2.00 |
| | sodium lauryl sulfate | 2.00 |
| | flavoring | 1.00 |
| | treatment composition | 1.00 |
| | bentonite | 0.50 |
| | sweetener | 0.10 |
| | water | bal. |
| 5. | calcium carbonate | 38.00% |
| | sorbitol | 20.00 |
| | sodium chloride | 9.00 |
| | mineral oil | 3.75 |
| | propylene glycol | 3.00 |
| | sodium lauryl sulfate | 1.00 |
| | flavoring | 1.00 |
| | treatment composition | 1.00 |
| | sweetener | 0.03 |
| | ethyl para-hydroxybenzoate | 0.02 |
| | butyl para-hydroxybenzoate | 0.01 |
| | water | bal. |
| 6. | silicic anhydride | 30.00% |
| | glycerin | 30.00 |
| | sorbitol | 20.00 |
| | mineral oil | 3.75 |
| | sodium lauryl sulfate | 2.00 |
| | sodium carboxymethyl cellulose | 1.00 |
| | treatment composition | 1.00 |
| | flavoring | 0.70 |
| | sweetener | 0.10 |
| | water | bal. |

Each of the above-noted formulations would be acceptable for use with the treatment composition of the present invention, although the skilled artisan will be readily familiar with other, equally suitable formulations.

b. Composition for Systemic Treatment

The treatment composition of the present invention can also be administered systemically, in other words, orally as in the form of capsules or tablets, parenterally as in the form of sterile solutions or suspensions, and in some cases intravenously in the form of sterile solutions.

The treatment composition can be administered orally, for example, with an inert diluent or with an edible carrier. It may be enclosed in gelatin capsules or compressed into tablets. For the purpose of oral therapeutic or prophylactic administration, the treatment composition may be incorporated with excipients and used in the form of tablets, pills, troches, elixirs, suspensions, syrups, wafers and the like. These preparations should contain at least about 4% by weight of the treatment composition, but may be varied depending upon the particular form and may conveniently be between about 4% and about 70% by weight of the unit. The amount of the treatment composition present is such that a therapeutically or prophylactically effective amount is used. The tablets, pills, capsules, troches and the like may also contain the following adjuvants: a binder such as microcrystalline cellulose, gum tragacanth or gelatin; an excipient such as starch or lactose; disintegrating agent such as alginic acid, corn starch an the like; a lubricant such as magnesium stearate; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to the above, a liquid carrier such as a fatty oil. Other dosage unit forms may contain other various materials which modify the physical form of the dosage unit, for example as coating. Thus, tablets or pills may be coated with sugar, shellac, or other enteric coating agents. A syrup may contain, in addition to the above, sucrose as a sweetening agent and certain preservatives, dyes and colorings and flavorings. Materials used in preparing these various compositions should be pharmaceutically acceptable and non-toxic in the amounts used.

For the purpose of parenteral administration, the treatment composition may be incorporated into a solution or suspension. These preparations should include at least about 0.1% by weight of the treatment composition, but may also be varied to be between 0.1% and about 50% by weight. The amount of the treatment composition should be that necessary to provide a therapeutically or prophylactically effective amount.

The solutions or suspensions may also include the following adjuvants: a sterile diluent such as water for injection, saline solution, fixed oils, polyethylene glycol, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid ("EDTA"); buffers such as acetates, citrates or phosphates; and agents for the adjustment of tonicity such as sodium chloride or dextrose. The parenteral preparation can be enclosed in ampules, disposable syringes or multiple dose vials made of glass or plastic.

Method of Use

The present invention also relates to the method of use of the treatment composition described above for the therapeutic or prophylactic treatment of dental plaque, calculus or gingivitis, or other periodontal diseases or conditions. Such method comprises either systemically administering or topically applying to the surfaces of the oral cavity (typically by brushing, rinsing or chewing) for a therapeutically or prophylactically effective time (although time is not relevant with respect to systemic treatment) a therapeutically or prophylactically effective amount of the treatment composition described above, usually, in the case of topical application, in association with a normally non-ingested carrier suitable for delivering the treatment composition to the oral cavity.

The term "therapeutically or prophylactically effective amount" as used herein refers to that amount which will significantly reduce the severity of the disease or condition being treated, or substantially reduce the potential for onset of such disease or condition, but will avoid serious disadvantageous side effects (at a reasonable benefit/risk ratio) according to sound medical judgment. The actual amount which comprises a therapeutically or prophylactically effective amount will vary according to whether therapeutic or prophylactic benefits are being sought, the particular disease or condition being treated, the severity of such disease or condition (if preexisting), the age and health of the patient, any additional therapy(ies) being undertaken, the particular method of treatment and carrier, and other factors which will be familiar to the skilled artisan (i.e., the attending physician or dentist). The amount for systemic treatment will generally be those amounts discussed above while for topical treatment, generally, the amount will be that amount which is provided by a carrier/treatment composition combination comprising about 0.25% to about 25.0% by weight of treatment composition.

The term "therapeutically or prophylactically effective time" as used herein refers to the amount of time necessary for the treatment composition of the present invention to be in contact with the surfaces of the oral cavity to provide the therapeutic or prophylactic benefits sought. It will be recognized that such time will vary according to those factors indicated above as well as by the amount of the treatment composition being applied to the surfaces of the oral cavity.

For the most effective use of the treatment composition of the present invention about 30 seconds to about 1 minute of topical application to the surfaces of the oral cavity is sufficient, especially when the carrier is a mouth rinse or mouthwash, although longer times will generally not be disadvantageous. Most often the usual time of application of the particular carrier being used will suffice for treatment of the oral cavity. For instance, if the carrier is a toothpaste composition, the normal teeth brushing time will generally provide therapeutically or prophylactically effective time of use of the composition of this invention.

Method of Making

The treatment composition of the present invention is typically prepared by isolating an unsaponifiable fraction which comprises at least about 80% of phytosterols from a crude vegetable oil. Exemplary of a procedure by which the treatment composition can be prepared generally comprises the following procedure:

(a) a "deodorizer distillate" is isolated from crude vegetable oil by treatment of the crude vegetable oil with steam at elevated temperatures (i.e., about 450° F. to about 500° F.) under vacuum (i.e., about 0.05 to about 0.02 atmospheres or about 3 to about 6 millimeters of mercury) for about 0.25 to about 3.0 hours. Isolation of the deodorizer distillate can be performed with conventional equipment, such as that available from the Votator Company of Chicago, Illinois. Suitable vegetable oils useful in preparing the unsaponifiable concentrates include wheat germ, avocado, corn and soybean oils, and mixtures thereof.

(b) the deodorizer distillate of step (a) is recovered and methylated to convert fatty acids or fatty acid esters of glycerol, sterols, or other higher alcohols, to methyl esters. Methylation generally involves reaction with methanol in the presence of a suitable catalyst, such as sodium methylate. For instance, 100 grams of deodorizer distillate are dissolved in 1000 milliliters of methanol. 1 gram of sodium methylate is then added and the mixture heated to reflux, and allowed to reflux for 1 hour. The mixture is then cooled to room temperature (about 25° C.) and 2 liters of water added. The organic layer is then allowed to separate and is recovered and dried.

(c) the recovered organic layer from step (b) is subjected to molecular distillation to (1) strip out methyl esters of fatty acids and other low boiling point materials; (2) remove the tocopherols; and (3) distill out the phytosterols, leaving as residue the higher boiling point materials. Molecular distillation can advantageously be performed in high vacuum stills, such as centrifugal molecular stills available from CVC Products Corp. of Chicago, Illinois. Approximate boiling points for the various fractions are:

tocopherols: 210° C.
methyl esters: 215° C.
glycerol: 220° C.
phytosterols: 240° C.

(d) the crude phytosterols product recovered in step (c) is then purified by crystallization from a mixed solvent, such as a mixture of acetone and methanol. For instance, 500 grams of crude phytosterols is dissolved in 600 milliliters of a mixture of equal parts of acetone and methanol by heating to boil under agitation. The mixture is then cooled slowly to about 10° C. and the crystals which have formed filtered off. The solvent is then removed from the recovered material by heating to the distillation temperature of the solvents. The molten phytosterols can then be recovered by allowing them to solidify.

(e) the purified phytosterol product can also be spray chilled (or prilled) to produce a powdered product, the treatment composition useful in the present invention. This can be accomplished by spraying the molten phytosterol concentrate of step (d) through a spray nozzle into chilled air in a spray tower.

The following example further illustrates and explains the present invention by detailing the treatment of periodontal diseases and conditions using the claimed treatment composition.

EXAMPLE I

A treatment composition was prepared according to the following procedure:

(a) a deodorizer distillate was isolated from crude soybean oil by treatment of the oil at about 450°–470° F. under about 4–5 mm of mercury vacuum for about 20 to 45 minutes using a distiller from Votator Company of Chicago, Illinois;

(b) the isolated deodorizer distillate was recovered and methylated by dissolving 100 grams of the deodorizer distillate in 1000 milliliters of methanol and adding 1 gram of sodium methylate. The mixture was then heated to reflux and allowed to reflux for about 1 hour, after which it was cooled to room temperature and 2 liters of distilled water added. The organic layer was allowed to separate and is recovered;

(c) the recovered organic layer was then subjected to molecular distillation in a centrifugal molecular still from CVC Products Corp. of Chicago, Illinois and the crude phytosterol product recovered by its boiling point;

(d) the recovered phytosterol product was then purified by dissolving 500 grams of the product in 600 milliliters of a 50/50 mixture of acetone and methanol and heating to a boil under agitation. The mixture was then cooled to about 10° C. overnight (i.e., about 16 hours) and the crystals which have formed filtered off. The solvent was then removed by heating to its distillation temperature, and the phytosterols recovered by allowing them to solidify; and (e) the purified phytosterol product was then prilled by spraying the molten phytosterol product through a spray nozzle into chilled air to form an unsaponifiable fraction comprising 84.48% phytosterols of which 21.3% is campesterol, 19.2% is stigmasterol, and 40.9% is beta-sitosterol, the remainder of which comprises cycloartenol, citrostadienol and the other, unidentified, phytosterols, to thusly form the treatment composition of this invention.

The treatment composition was then mixed with mineral oil and incorporated into a toothpaste having the following formulation (by parts by weight):

active ingredient: 1.00
mineral oil: 3.75
sorbitol: 52.90
water: 21.31
hydrated silica: 15.50
flavors and dyes: 1.50
trisodium phosphate: 1.10
titanium dioxide: 1.00
monosodium phosphate: 0.90
sodium lauryl sulfate: 0.50
thickeners: 0.50
sweetener: 0.30
sodium fluoride: 0.24 to form a toothpaste having about 1.0% treatment composition. A control toothpaste formulation was prepared having no treatment composition and 4.75 parts by weight of mineral oil.

An 8 week double blind study was then undertaken to compare the thusly prepared toothpastes. The parameters studied were plaque, gingivitis, calculus, bleeding and staining and measurements taken by conventional techniques familiar to the skilled artisan. No side effects from the use of the studied toothpastes were observed on any of the soft or hard tissue during any of the examinations during the study. The results are set out in Table 1.

TABLE 1

| Condition or Disease Being Measured | Percent Change from Baseline | |
|---|---|---|
| | Active | Control |
| Plaque | | |
| Buccal | −20.1* | −6.2 |
| Lingual | −9.3 | −19.4* |
| Gingivitis | | |
| Buccal Smooth | −55.2* | −12.5 |
| Buccal Interproximal | −37.5* | −28.6* |
| Lingual Smooth | −27.9* | −19.1 |
| Lingual Interproximal | −26.6* | −23.2* |
| TOTAL | −32.0* | −22.0* |
| Calculus** | +6.8 | +14.0* |
| Bleeding | −46.4* | −36.8* |

TABLE 1-continued

| Condition or Disease Being Measured | Percent Change from Baseline | |
| --- | --- | --- |
| | Active | Control |
| Staining | −2.8 | +2.8 |

*denotes that result is statistically different from the baseline
**a positive result indicates the presence of calculus, therefore, the lower the number, the more effective the treatment It is clear from the results in Table 1 that the use of the treatment composition of the present invention provides the therapeutic and prophylactic treatment of plaque, gingivitis and calculus without significant staining or bleeding problems. In fact, the fact that the buccal and lingual interproximal results are significantly different from the baseline indicates that the treatment composition is able to reach and treat area of the oral cavity where ordinary brushing usually misses.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

I claim:

1. A composition for the therapeutic or prophylactic treatment of dental plaque, calculus or gingivitis in humans and animals, which composition consists essentially of (1) an active treatment composition consisting essentially of at least about 80% by weight phytosterols, said phytosterols comprising at least about 40% by weight sitosterol, about 20% to about 45% by weight campesterol and about 3% to about 25% by weight stigmasterol, and (2) a normally non-ingested carrier in association with said active treatment composition suitable for delivering said active treatment composition to the oral cavity.

2. The composition of claim 1 wherein said treatment composition consists essentially of about 40% to about 60% by weight of sitosterol, about 20% to about 33% by weight of campesterol and about 15% to about 25% by weight of stigmasterol.

3. The composition of claim 1 wherein said carrier is comprised of one or more components selected from the group consisting of surfactants, flavoring agents, sweeteners, abrasives, humectants, sudsing agents, chelating agents, fluoride-containing agents, antiseptics, germicides, astringents, thickeners, coloring agents, emulsifiers, water, alcohols, effervescing agents, gums, dental floss and mixtures thereof.

4. The composition of claim 3 wherein said carrier comprises toothpaste or toothpaste gel.

5. A composition for the therapeutic or prophylactic treatment of dental plaque, calculus, or gingivitis, which composition comprises an unsaponifiable fraction isolated from crude vegetable oil, said unsaponifiable fraction comprising at least about 80% of phytosterols, said phytosterols comprising at least about 40% by weight sitosterol, about 20% to about 45% by weight campesterol, and about 3% to about 25% by weight stigmasterol.

6. The composition of claim 5 wherein said unsaponifiable fraction is prepared by:

(a) isolating a deodorizer distillate from crude vegetable oil;
(b) methylating said deodorizer distillate;
(c) subjecting said methylated deodorizer distillate to molecular distillation to isolate the phytosterols; and
(d) purifying the isolated phytosterols by crystallizing from a mixed solvent to provide an unsaponifiable fraction comprising at least about 80% phytosterols.

7. The composition of claim 6 wherein said unsaponifiable fraction comprises at least about 94% of phytosterols.

8. The composition of claim 5 wherein said crude vegetable oil is selected from the group consisting of wheat germ oil, avocado oil, soybean oil and corn oil.

9. The composition of claim 5 wherein said unsaponifiable fraction comprises about 40% to about 60% by weight of sitosterol, about 20% to about 33% by weight of campesterol and about 15% to about 25% by weight of stigmasterol.

10. The composition of claim 5 wherein said unsaponifiable fraction is associated with a normally non-ingested carrier suitable for delivery of the composition to the oral cavity.

11. The composition of claim 10 wherein said carrier is comprised of one or more components selected from the group consisting of surfactants, flavoring agents, sweeteners, abrasives, humectants, sudsing agents, chelating agents, fluoride-containing agents, antiseptics, germicides, astringents, thickeners, coloring agents, emulsifiers, water, alcohols, effervescing agents, gums, dental floss and mixtures thereof.

12. The composition of claim 11 wherein said carrier comprises toothpaste or toothpaste gel.

13. A method for the treatment or prevention of dental plaque, calculus or gingivitis in humans and animals comprising either systemically or topically treating the oral cavity with a therapeutically or prophylactically effective amount of an active treatment composition which consists essentially of at least about 80% by weight of phystosterols, said phytosterols comprising at least about 40% by weight sitosterol, about 20% to about 45% by weight campesterol and about 3% to about 20% by weight stigmasterol.

14. The method of claim 13 wherein said treatment composition comprises about 40% to about 60% by weight of sitosterol, about 20% to about 33% by weight of campesterol and about 15% to about 25% by weight of stigmasterol.

15. The method of claim 13 wherein said treatment composition comprises at least about 94% by weight of phytosterols.

16. The method of claim 13 wherein said oral cavity is treated by topically applying to the surfaces of the oral cavity for a therapeutically or prophylactically effective time a therapeutically or prophylactically effective amount of said treatment composition.

17. The method of claim 16 wherein said treatment composition is associated with a normally non-ingested carrier delivery of said treatment composition to the oral cavity.

18. The method of claim 17 wherein said carrier is comprised of one or more components selected from the group consisting of surfactants, flavoring agents, sweeteners, abrasives, humectants, sudsing agents, chelating agents, fluoride-containing agents, antiseptics, germicides, astringents, thickeners, coloring agents, emulsifiers, water, alcohols, effervescing agents, gums, dental floss and mixtures thereof.

19. The method of claim 18 wherein said carrier comprises toothpaste or toothpaste gel.

20. The method of claim 13 wherein said treatment composition is prepared by isolation from a crude vegetable oil.

21. The method of claim 20 wherein said crude vegetable oil is selected from the group consisting of wheat germ oil, avocado oil, soybean oil and corn oil.

22. A method for the treatment or prevention of dental plaque, calculus or gingivitis in humans and animals comprising either systemically or topically treating the oral cavity with a therapeutically or prophylactically effective amount of a treatment composition which consists essentially of at least about 80% by weight phytosterol, said phytosterols comprising of at least about 40% by weight sitosterol, about 20% to about 45% by weight campesterol and about 3% to about 26% by weight stigmasterol.

23. The method of claim 22 wherein said treatment composition comprises about 40% to about 60% by weight of sitosterol, about 20% to about 33% by weight of campesterol and about 15% to about 25% by weight of stigmasterol.

24. The method of claim 22 wherein the oral cavity is treated by topically applying to the surfaces of the oral cavity for a therapeutically or prophylactically effective time a therapeutically or prophylactically effective amount of said treatment composition.

25. The method of claim 24 wherein said treatment composition is associated with a normally non-ingested carrier suitable delivery of said treatment composition to the oral cavity.

26. The method of claim 25 wherein said carrier is comprised of one or more components selected from the group consisting of surfactants, flavoring agents, sweeteners, abrasives, humectants, sudsing agents, chelating agents, fluoride-containing agents, antiseptics, germicides, astringents, thickeners, coloring agents, emulsifiers, water, alcohols, effervescing agents, gums, dental floss and mixtures thereof.

27. The method of claim 26 wherein said carrier comprises toothpaste or toothpaste gel.

28. The method of claim 22 wherein said treatment composition is prepared by isolation from a crude vegetable oil.

29. The method of claim 28 wherein said crude vegetable oil is selected from the group consisting of wheat germ oil, avocado oil, soybean oil and corn oil.

* * * * *